United States Patent [19]

Högberg et al.

[11] 4,418,065
[45] Nov. 29, 1983

[54] HALOPHENYL-PYRIDYL-ALLYLAMINE DERIVATIVES AND USE

[75] Inventors: Thomas Högberg, Järna; Tomas de Paulis, Södertälje; Svante B. Ross, Södertälje; Carl B. J. Ulff, Södertälje, all of Sweden

[73] Assignee: Astra Lakemedel Aktiebolag, Sodertalje, Sweden

[21] Appl. No.: 232,043

[22] PCT Filed: Nov. 14, 1980

[86] PCT No.: PCT/SE80/00286
§ 371 Date: Jul. 16, 1981
§ 102(e) Date: Jan. 13, 1981

[87] PCT Pub. No.: WO81/01407
PCT Pub. Date: May 28, 1981

[30] Foreign Application Priority Data
Nov. 16, 1979 [SE] Sweden ............................ 7909514

[51] Int. Cl.³ .................. A61K 31/44; C07D 213/38
[52] U.S. Cl. .................................. 424/263; 546/333
[58] Field of Search ..................... 546/333; 424/263

[56] References Cited
U.S. PATENT DOCUMENTS

| 2,676,964 | 4/1954 | Sperber et al. ............... | 260/256.4 |
| 3,354,206 | 11/1967 | Wendler et al. ............... | 260/556 |
| 3,396,224 | 8/1968 | Van Heyningen ............... | 426/263 |
| 3,423,510 | 1/1969 | Sigg ........................... | 424/263 |
| 3,471,505 | 10/1969 | Laszlo ......................... | 260/297 |
| 3,928,369 | 12/1975 | Berntsson et al. ............. | 260/296 |
| 3,928,613 | 12/1975 | Berntsson et al. ............. | 424/263 |
| 3,951,961 | 4/1975 | Ujvari et al. .................. | 260/240 |
| 4,094,908 | 6/1978 | Toth et al. .................... | 260/570 |
| 4,186,202 | 1/1980 | Carlsson et al. ................ | 424/263 |
| 4,216,328 | 8/1980 | Bamberg et al. ................ | 546/329 |

FOREIGN PATENT DOCUMENTS

| 781105 | 3/1972 | Belgium . |
| 322 | 1/1979 | European Pat. Off. . |
| 966534 | 8/1957 | Fed. Rep. of Germany . |
| 2206942 | 1/1977 | France . |
| 75/6893 | 2/1977 | South Africa . |
| 76/05573-0 | 11/1977 | Sweden . |
| 76/05779-3 | 11/1977 | Sweden . |
| 388854 | 3/1979 | Sweden . |
| 409706 | 9/1979 | Sweden . |
| 409860 | 9/1979 | Sweden . |
| 409861 | 9/1979 | Sweden . |
| 850298 | 10/1960 | United Kingdom . |
| 1366241 | 9/1974 | United Kingdom . |
| 1429068 | 3/1976 | United Kingdom . |
| 1530804 | 11/1978 | United Kingdom . |

OTHER PUBLICATIONS

Gordon, "Psychopharmacological Agents" vol. 1, pp. 54-55 (1964).
Hoffsommer et al., "Synthesis of Amitriptyline and Related Substances" Journal of Org. Chem. 28(7) pp. 1751-1753 (1963).
Chem. Abstracts 46:2055; 58:9031; 76:59467; 86:139786; 87:133285.

Primary Examiner—Richard Raymond
Attorney, Agent, or Firm—Brumbaugh, Graves, Donohue & Raymond

[57] ABSTRACT

Compounds of the formula

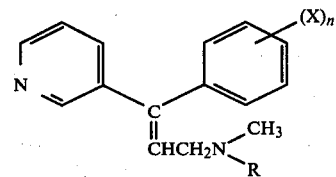

wherein R is H or $CH_3$, n is 1 or 2 and X is F, Cl, Br, I bound in an optional position to the phenyl group, provided that when X is Br it is bound in a position other than the 4 position, processes for their preparation and phrmaceutical preparations, methods of treatment employing such compounds. The compounds are useful for therapeutic treatment of various kinds of depressive conditions.

24 Claims, No Drawings

HALOPHENYL-PYRIDYL-ALLYLAMINE DERIVATIVES AND USE

DESCRIPTION

1. Technical Field

The present invention relates to new compounds having therapeutic activity and to methods for their preparation. The invention also relates to the preparation of pharmaceutical preparations containing at least one of the compounds and to methods for their pharmacological use.

2. Background Art

It is known from the literature that certain 1,1-diphenyl-3-aminoprop-1-enes, such as the compound having the formula

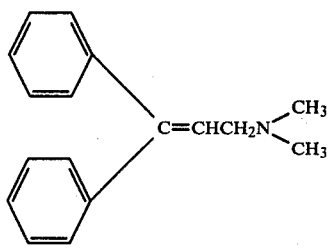

have an antidepressive effect, of J. Med. Chem. 14, 161–4 (1971). Compounds having the formula

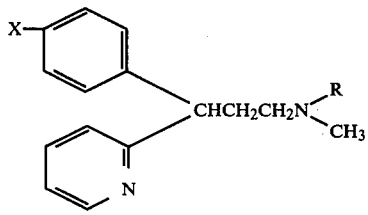

wherein X is chlorine or bromine and R is hydrogen or methyl, are described to have antidepressive effect, cf. U.S. Pat. No. 3,423,510. From the literature it is also known that compounds having the formula

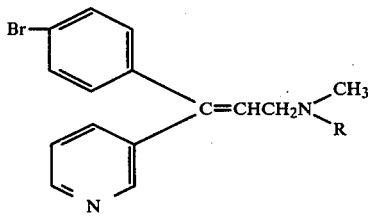

have antidepressive activity in animal models, cf. Belgian Patent Specifications No. 781,105 and No. 835,802.

DISCLOSURE OF INVENTION

(a) General outline

A main object of the present invention is to obtain new compounds having a good antidepressive effect. A further object of the invention is to obtain compounds having an antidepressive effect, and giving rise to only minor side-effects, in particular arrhythmogenic effects and anticholinergic effects. A further object is to provide antidepressive compounds useful for treatment of various kinds of depressions e.g. depressions connected with insufficient synaptic amounts of 5-hydroxytryptamine, noradrenaline or both. Further objects of the invention will be evident from the following description.

The compounds of the invention are characterized by the formula

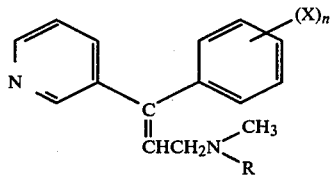

wherein R is H or CH$_3$, n is 1 or 2, and X is a halogen selected from F, Cl, Br I and CF$_3$ bound in an optional position to the phenyl group provided that when X is Br it is bound in a position other than the 4 position.

Pharmaceutically acceptable salts of these compounds are included within this invention.

Due to the lack of free rotation in the double bond the compounds of this invention may exist in different stereoisomeric forms, that is in cis-trans isomers or, according to the IUPAC nomenclature (J. Org. Chem. 35, 2849–2867, September 1970), in an E-form and a Z-form. The compound may be used therapeutically as a mixture of geometrical isomers or in pure E or Z form. The pure geometrical isomers may be prepared from an isomer mixture, from an isomer-pure starting material or directly by a stereoselective synthesis.

The compounds of this invention may be administered in the form of free bases or their salts with non-toxic acids. Some typical examples of these salts are the hydrobromide, hydrochloride, phosphate, sulphate, citrate, tartrate, malate and maleate.

(b) Pharmaceutical preparations

In clinical practice the compounds of the present invention will be normally administered orally, rectally or by injection, in the form of pharmaceutical preparations comprising the active ingredient either as a free base or as a pharmaceutically acceptable, non-toxic acid addition salt, e.g. as the hydrochloride, hydrobromide, lactate, acetate, sulphate or sulphamate in association with a pharmacetically acceptable carrier. Accordingly, terms relating to the novel compounds of this invention whether generical or specifical are intended to include both the free amine base and the acid addition salts of the free base, unless the context in which such terms are used, e.g. in the specific examples would be inconsistent with the broad concept. The carrier may be a solid, semisolid or liquid diluent, or a capsule. These pharmaceutical preparations constitute a further aspect of this invention.

Usually the active substance will constitute from 0.1 to 99% by weight of the preparation, more specifically from 0.5 to 20% by weight for preparations intended for injection and from 2 to 50% by weight for preparations suitable for oral administration.

To produce pharmaceutical preparations containing a compound of the invention in the form of dosage units for oral application, the selected compound may be mixed with a solid pulverulent carrier, e.g. lactose, saccharose, sorbitol, mannitol, starches such as potato starch, corn starch or amylopectin, cellulose derivatives, or gelatine, and a lubricant such as magnesium stearate, calcium stearate or polyethylene glycol waxes, and then compressed to form tablets. If coated tablets are required, the cores, prepared as described above, may be coated with a concentrated sugar solution which may contain, e.g. gum arabic, gelatine, talcum or titanium dioxide. Alternatively, the tablet can be coated with a lacquer dissolved in a readily volatile organic solvent or mixture of organic solvents. Dyestuffs may be added to these coatings in order to readily distinguish between tablets containing different active substances of different amounts of the active compound.

For the preparation of soft gelatine capsules (pearl-shaped closed capsules) consisting of gelatine and for example, glycerol or similar closed capsules, the active substance may be admixed with a vegetable oil, Hard gelatine capsules may contain granulates of the active substance in combination with solid, pulverulent carriers such as lactose, saccharose, sorbitol, mannitol, starches (e.g. potato starch, corn starch or amylopectin), cellulose derivatives or gelatine.

Dosage units for rectal application can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example solutions containing from about 0.2% to about 20% by weight of the active substance herein described, the balance being sugar and a mixture of ethanol, water, glycerol, and propyleneglycol. Optionally such liquid preparations may contain colouring agents, flavouring agents, saccharine and carboxymethylcellulose as a thickening agent.

Solutions for parenteral applications by injection can be prepared in an aqueous solution of a water-soluble pharmaceutically acceptable salt of the active substance preferably in a concentration of from about 0.5% to about 10% by weight. These solutions may also contain stabilizing agents and/or buffering agents and may conveniently be provided in various dosage unit ampoules.

Suitable daily doses of the compounds of the invention at therapeutically treatment is 5 to 500 mg at peroral administration, preferably 50 to 250 mg and 1 to 100 mg at parenteral administration, preferably 10 to 50 mg.

(c) Preferred embodiment

The preferred compounds of the invention are those compounds of formula I wherein R is H. A distinct embodiment of the invention is constituted by the compounds wherein n is 1. Compounds of formula I wherein X represents F or I are to be specifically mentioned. Among the compounds of formula I the geometrical isomers of compounds wherein X is 3-Cl or 4-Cl and R is $CH_3$ are to be mentioned as possessing an unexpected pharmacological profile.

Further, among the compounds of the invention the following are to be mentioned:

The group of compounds having a substituent X in the 2 position of the phenyl group comprising 3-(2-bromophenyl)-N,N-dimethyl-3-(3-pyridyl)-allylamine,
3-(2-bromophenyl)-N-methyl-3-(3-pyridyl)-allylamine,
3-(2,4-dichlorophenyl)-N,N-dimethyl-3-(3-pyridyl)-allylamine,
3-(2,4-dichlorophenyl)-N-methyl-3-(3-pyridyl)-allylamine, and
E-3-(2,4-dichlorophenyl)-N-methyl-3-(3-pyridyl)-allylamine;

and the group of iodine or fluorine substituted compounds comprising 3-(4-iodophenyl)-N,N-dimethyl-3-(3-pyridyl)-allylamine,
3-(4-fluorophenyl)-N-methyl-3-(3-pyridyl)-allylamine, and the group of pure Z isomeric compounds comprising Z-3-(4-chlorophenyl)-N,N-dimethyl-3-(3-pyridyl)-allylamine, and
Z-3-(4-chlorophenyl)-N-methyl-3-(3-pyridyl)-allylamine;

as well as the single members of said groups.

The pure or substantially pure geometrical isomers of the compounds of the invention constitute a further preferred embodiment. Especially preferred are the substantially pure isomers in which the pyridyl group and the mono- or di-methylamino groups are in cis configuration. In the IUPAC nomenclature such compounds are E forms when a substituent X is in the 2 position and Z forms in other cases.

(d) Methods of preparation

A. Dehydration of a compound of the formula

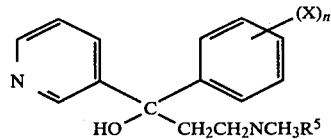

wherein n is 1 or 2, X is as defined above and $R^5$ is H, $CH_3$ or a removable protective group such as benzyl, trityl, 4,4'-dimethoxybenzhydryl, benzyloxycarbonyl, tert-butyloxycarbonyl, 9-anthrylmethyloxycarbonyl, or vinyloxycarbonyl, to a compound of the formula I, whereby a removable protective group $R^5$, when occurring, is split off by reduction or hydrolysis before, during or after the dehydration.

The dehydration of the starting material may for example be done by means of treatment with sulphuric acid and heating of the reaction mixture. The dehydration of the starting material may also be done by means of other types of acid-catalysis, such as by means of hydrochloric acid, phosphoric acid, potassium hydrogen sulphate, or oxalic acid. Other methods for the dehydration of the starting material to the formation of a compound of the formula I are dehydration using phosphoroxychloride in pyridine, and dehydration with thionylchloride in pyridine.

Also a catalytic dehydration of the starting material may be used. The dehydration is in this case carried out at a temperature of about 300° to 500° C. using a catalyst such as kaolin, aluminium or aluminium oxide.

B. Treating a compound of the formula

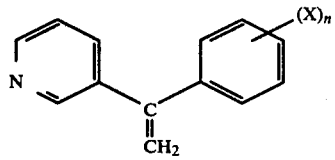

with formaldehyde and an amine of the formula

whereby n and X are as defined above and $R^2$ is $CH_3$ or a removable protective group such as those mentioned under A above, to the formation of a compound of formula I.

C. Amination of a compound of the formula

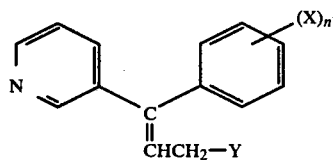

wherein n and X are as defined above and Y is a leaving group with an amine $HNCH_3R^5$ wherein $R^5$ is as defined above, to the formation of a compound of the formula I.

Illustrative examples of Y are halogens such as Cl, Br and I or sulphonates such as methanesulphonate, toluenesulphonate and benzenesulphonate or ester functions such as a lower alkanoyloxy group, preferably having 2–4 carbon atoms, such as acetoxy.

D. Mono- or di-methylation of a primary amine or monomethylation of a secondary amine all of the formula

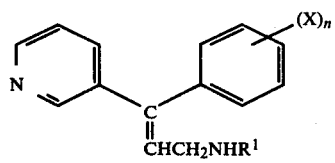

wherein n and X are as defined above and $R^1$ is H or $CH_3$, to the formation of a compound of the formula I.

In the preparation of a secondary amine a protective acyl or sulphonyl group may first be introduced at the amino group. Such protective group is finally split off by hydrolysis.

E. Converting a compound of the formula

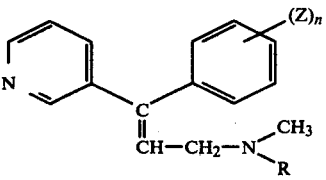

wherein R is as defined above, n is 1 or 2, and Z is a replaceable moiety such as Cl, Br or I in an optional position, with position limitations as set out for X in formula I, into a compound of the formula I wherein X is Cl, Br or I in the same position as Z, however, X being different from Z. The conversion may be carried out by first converting the starting material to a metal-organic intermediate by reaction with e.g. butyl lithium and reacting the intermediate, e.g. a compound of the above formula wherein Z is Li, with the desired halogen such as $Cl_2$, $Br_2$ or $I_2$ or a synthetic equivalent thereto, such as hexachloroethane, 2,3-dibromo-2,3-dimethylbutane or methylene iodide.

F. Conversion of a ketone of the formula

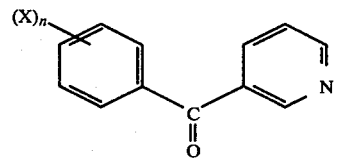

with a phosphorous ylide prepared either in situ or presynthesized by reaction of a compound of the formula

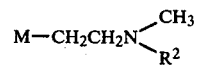

whereby X and $R^2$ are as defined above and M is $R_3{}^3P+$, $R_3{}^4P+$, $(R^4O)_2P(O)$, $R_2{}^3P(O)$, $(R_2{}^4N)_2P(O)$ or $(R^4O)_2P(S)$, and $R^3$ is a possibly substituted phenyl group and $R^4$ is an alkyl group having 1–5 carbon atoms, whereby an an-ion such as a halogen e.g. $Br^-$ is present when M is $R_3{}^3P+$ or $R_3{}^4P+$, with a base such as butyl- or phenyllithium, sodium amide, sodium hydride or sodium alkoxide, to the formation of a compound of formula I.

G. Reductive amination of an aldehyde or carboxylic acid of the formula

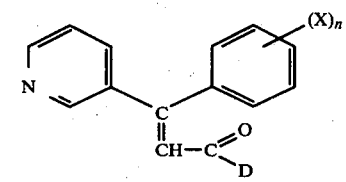

wherein D is H or OH, with methylamine or dimethylamine in the presence of a reducing agent, to the formation of a compound of formula I. The reducing agent can be e.g. sodium cyanoborohydride, sodium borohydride, formic acid, formamides or alcoholic potassium hydroxide. When D is OH sodium borohydride is preferably used with e.g. tetrahydrofuran as solvent. When D is H sodium cyanoborohydride may be used in an alcoholic solution.

H. Palladium catalyzed amination of compounds of the following formulas

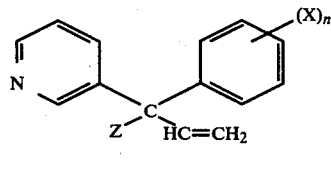

or

-continued

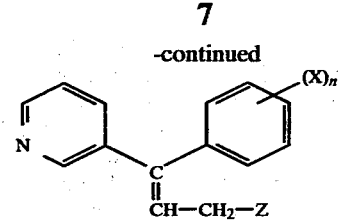
XII wherein Z is a leaving group such as hydroxy, alkoxy, alkanoyloxy such as acetoxy, or chloro, with dimethylamine or methylamine. Generation of the intermediate π-allylpalladium complexes of the formula

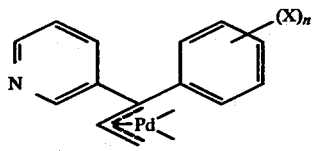

may be accomplished with a catalyst such as Pd(Ph$_3$P)$_4$, Pd black, Pd(AcAc)$_2$ or Pd(OAc)$_2$ preferably in the presence of a ligand such as Ph$_3$P or 1,2-bis(diphenylphosphino)ethane.

(e) Intermediates

For the preparation of the compounds of formula I it has been found that certain hitherto unknown compounds may be valuable.

When preparing the compounds of formula I according to process A compounds of the formula

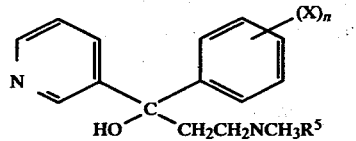
II wherein R, n and X are as defined above are used as starting materials.

These starting materials may be prepared by reacting a compound of the formula

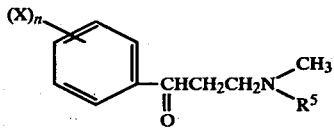
XIII in which formula n, X and R$^5$ have the meanings indicated above, with 3-pyridyllithium, whereafter when R denoting H is desired, a protective group R$^5$ is split off.

Alternatively such protective group may be split off after or during dehydration to a corresponding allylamine, whereby the splitting gives a secondary amine of formula I.

When preparing compounds of the formula I according to process B compounds of the formula

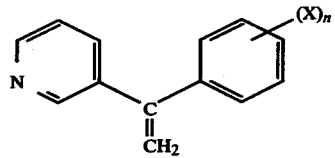
III wherein n and X are as defined above, are used as starting material. This starting material can be prepared by dehydration of

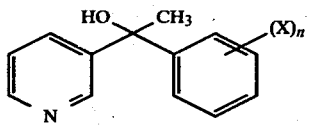
XIV or by a Wittig reaction of the ketone

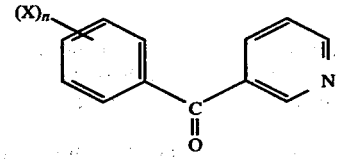
VIII

The intermediates constitute a further aspect of the invention.

When preparing the compounds of the formula I according to process C compounds of the formula

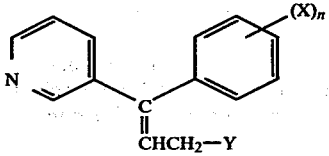
V wherein Y is a leaving group are used as starting material.

This starting material can be prepared according to the reaction scheme

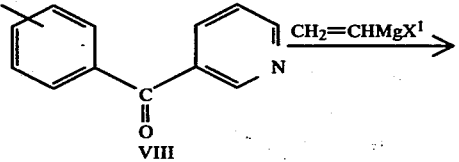

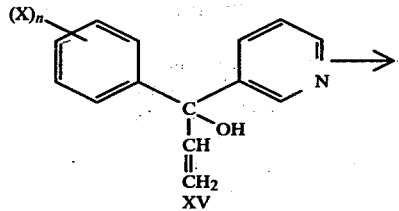
XV

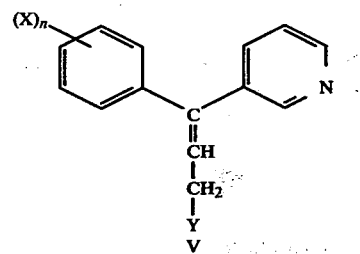
V wherein n, X and Y are as defined above and X$^1$ is Cl, Br or I.

The allylic tertiary alcohol of formula XV is a further useful novel intermediate. In addition to its utility for preparation of the starting material for process C it is also useful in other reaction routes finally producing the compound of formula I, such as process G, as will be further described below. Further, an alkancarboxylic ester of the tertiary alcohol XV is a useful intermediate, as further described in other parts of this specification. The tertiary alcohol XV is thus obtainable by a Grignard synthesis from the corresponding ketone. An allylic rearrangement introducing the group Y may be produced by employing one of the following reagents; aqueous hydrochloric acid, aqueous hydrobromic acid, phosphorus trichloride, thionylchloride, phosphorus pentachloride or another halogenating agent or methylsulfonic or toluenesulfonic acid.

When preparing the compound of the formula I according to process D a compound of the formula

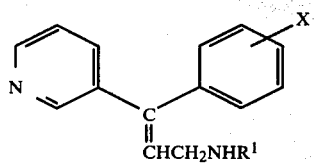   VI is used as starting material. The preparation of this compound is described in paragraph (d), when $R^1$ is $CH_3$. When $R^1$ is H processes in analogy with processes A or C may be employed.

Starting materials for process E are obtainable by processes known in the art, or described in paragraph (d) above.

Starting materials for process F are obtainable by processes known in the art.

When preparing the compound of formula I according to process G a compound of the formula

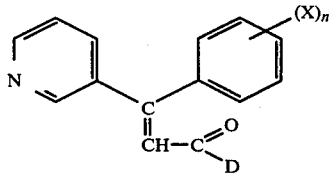   X in which formula D is H or OH and n and X are as defined above, is used as starting material.

The aldehyde (D is H) starting material may be prepared by oxidation of a compound of formula

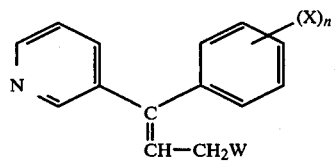   XVI wherein W is OH or a leaving group Y, NR'R", NR'H, $NH_2$ or

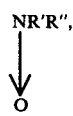

wherein R' and R" are alkyl groups having 1–4 carbon atoms, with reagents such as manganese dioxide, dimethyl sulfoxide, silver(I), silver(II), iron(III), chromium trioxide reagents, aluminium alkoxides, nickel peroxide, lead tetraacetate and 2,3-dichloro-5,6-dicyanobenzoquinone or by oxidation in one step from a compound of the formula XV above with an appropriate reagent mentioned above, such as chromic acid/sulfuric acid.

The carboxylic acid (D is OH) starting material may be prepared by further oxidation of the aldehyde mentioned above or by direct oxidation of a compound of formula XVI above wherein W preferably represents a hydroxy group with reagents like nickel peroxide, silver oxide, selenium dioxide, manganese dioxide, chromic acid, permanganate or $Pt/O_2$. Alternatively, the acrylic acids (XI, D=OH) may be prepared by dehydration and hydrolysis of

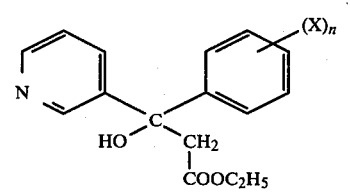   XVII which are obtainable by a Reformatsky reaction from 3-pyridyl aryl ketones.

The intermediate alcohol of formula XVI may be prepared by acid catalyzed rearrangement of the corresponding tertiary allylic alcohol of formula XV with acids such as sulfuric acid, phosphoric acid or p-toluenesulfonic acid, and if required subsequent introduction of a leaving group or amino function as described above.

The starting materials of formulas XI and XII employed in process H are obtainable in the manner described for compounds XV and V above with introduction of the group Z when required.

The allylic tertiary alcohols used in the different processes described above are consolidated in formula XI above. In said formula the group Z may contain 1–4 carbon atoms.

(f) Working examples

PREPARATION OF INTERMEDIATES

Example A 2-(3-Chlorobenzoyl)-N,N-dimethylethylamine hydrochloride

3-Chloroacetophenone (35.8 g, 0.23 mol), dimethylamine hydrochloride (28.1 g, 0.345 mol), paraformaldehyde (13.8 g, 0.46 mol) and concentrated hydrochloric acid (0.75 ml) were refluxed in 60 ml ethanol for 5 h.

After cooling the precipitated hydrochloride was collected and dried in vacuo. Yield 42.3 g (86%). M.p. 189°–191° C. Recrystallisation from ethanol/water (15:1) gave the pure product. M.p. 193°–195° C.

3-(3-Chlorophenyl)-N,N-dimethyl-3-hydroxy-3-(3-pyridyl)propylamine

To a solution of butyllithium (61 ml of a 1.5 M solution in hexane, 92 mmol) in 25 ml ether at −50° to −60° C. 3-brompyridine (15.2 g, 96 mmol) was added in 40 min. After stirring for 15 min 2-(3-chlorophenyl)-N,N-dimethylethylamine (16.9 g, 80 mmol) in 25 ml ether was added at about −50° C. in 1 h. After stirring at −40° to −50° C. for 2 h the mixture was poured on 120 ml water and 14 ml concentrated hydrochloric acid. The pH was adjusted to about 6 and the solution extracted with petroleum ether (80°–110° C.).

The aqueous phase was made alkaline (pH 10.5) and extracted with ether. The ether phase was dried and evaporated to yield 21.4 g brown oil which crystallized. The solid was triturated with petroleum ether (80°–110° C.) and then recrystallized from petroleum ether (80°–110° C.) to give 9.6 g (41%) white crystals. M.p. 102°–104° C. Preparation of an end compound from the intermediate obtained is described in Example 1.

Example B 1-(4-Chlorophenyl)-1-(3-pyridyl)-2-propen-1-ol

A solution of vinylbromide (11.8 g, 110 mmol) in 40 ml tetrahydrofuran was added to a mixture of magnesium (2.79 g, 115 mmol) in 20 ml tetrahydrofuran under a nitrogen atmosphere at 50° to 60° C. After reflux for 1 h 3-(4-chlorobenzoyl)pyridine (21.8 g, 0.100 mol) in 100 ml tetrahydrofuran was added at 10° C. After stirring for 1 h a solution of 8 g ammonium chloride in 40 ml water was added and the mixture filtrated. The organic phase was dried over sodium sulphate and evaporated to give 29.4 g of a red oil containing 20% unreacted starting ketone. This crude product was used directly in the next step (Example C).

Example C

3-Chloro-1-(4-chlorophenyl)-1-(3-pyridyl)-1-propene

A solution of crude 1-(4-chlorophenyl)-1-(3-pyridyl)-2-propen-1-ol (40 mmol) in 100 ml methylene chloride was added dropwise to a suspension of phosphorus pentachloride (12.4 g, 60 mmol) at 10° C. After stirring for 1 h at room temperature the solution was washed with 50 ml water at 0° to 10° C. The solution of the crude title compound was used in the following aminations, i.e. Example 2 and 3.

Example D 1-(4-Chlorophenyl)-1-(3-pyridyl)-2-propen-1-ol

A solution of vinylbromide (38.4 g, 359 mmol) in 100 ml tetrahydrofuran was added to a mixture of magnesium (9.15 g, 377 mmol) in 40 ml tetrahydrofuran under a nitrogen atmosphere at 50° to 60° C. After reflux for 1 h 3-(4-chlorobenzoyl)pyridine (62.4 g, 287 mmol) in 250 ml tetrahydrofuran was added at 10° C. After stirring for 1 h a solution of 20 g ammonium chloride in 100 ml water was added and the mixture filtered. The organic phase was evaporated and the residue taken up in ether and treated with charcoal. After filtration the solvent was evaporated to give 62.6 g (89%) of a brownish oil which solidified. Recrystallisation from toluene gave a product having m.p. 82.5°–84° C.

The allylic alcohols according to Examples E–H were prepared in analogy with the above procedure in Example D. Preparation of end compounds from the intermediates is described in Examples 4–10.

Example E 1-(4-Fluorophenyl)-1-(3-pyridyl)-2-propen-1-ol. 85% yield. Oil.

Example F 1-(2-Bromophenyl)-1-(3-pyridyl)-2-propen-1-ol. 86% yield. M.p. 111°–112° C.

Example G 1-(3-Bromophenyl)-1-(3-pyridyl)-2-propen-1-ol. 90% yield. Oil.

Example H 1-(2,4-Dichlorophenyl)-1-(3-pyridyl)-2-propen-1-ol. 88% yield. M.p. 111°–112° C.

Example I (Z)-3-(4-Chlorophenyl)-3-(3-pyridyl)-2-propenal

A mixture of 2.5 mmol 3-(4-chlorophenyl)-N,N-dimethyl-3-(3-pyridyl)allylamine and 7 g manganese dioxide in 25 ml chloroform was stirred at reflux for 1.5 h under nitrogen. An additional portion of 5 g manganese dioxide was added and after stirring for another 2 h. The mixture was filtered and the solvent evaporated to leave 0.58 g (84%) of a yellow oil.

TLC revealed no starting amine. $^1$H NMR (CDCl$_3$) showed the typical signals at δ6.7 (d, J=8 Hz, vinyl), 8.7 (m, 2-pyridyl), 8.85 (dd, 6-pyridyl) and 9.6 (d, J=8 Hz, aldehyde) ppm. The crude product was used directly in the reductive methylamination according to Example 14 below.

Example J 3-(4-Chlorophenyl)-3-(3-pyridyl)-2-propen-1-ol 1-(4-Chlorophenyl)-1-(3-pyridyl)-2-propen-1-ol (0.33 g) was stirred in 25 ml 2 M sulfuric acid overnight at 50° C. The reaction mixture was made alkaline with 45% sodium hydroxide and extracted with ether. The ethereal layer was dried (MgSO$_4$) and evaporated to give 0.30 g of the title compound as an oil. $^1$H NMR (CDCl$_3$) revealed an approximate Z/E ratio of 60/40:δ3.8 (Br, OH), 4.20 and 4.25 (two doublets, allyl), 6.37 and 6.30 (two triplets, vinyl), 6.9–7.6 (aromatic) and 8.3–8.6 (multiplet, 2,6-pyridyl). This crude product was used directly in the oxidation step according to Example K.

Example K 3-(4-Chlorophenyl)-3-(3-pyridyl)-2-propenal

A mixture of 0.30 g 3-(4-chlorophenyl)-3-(3-pyridyl)-2-propen-1-ol and 1.5 g manganese dioxide in 15 ml chloroform was stirred overnight at room temperature under nitrogen. Filtration and evaporation of the solvent gave 0.30 g of a yellow oil, which contained the isomeric aldehydes in a Z/E ratio of circa 60/40 according to NMR. The crude product was used directly in the reductive dimethylamination according to Example 15.

Example L

3-Acetoxy-3-(4-chlorophenyl)-3-(3-pyridyl)-1-propene

A mixture of 1-(4-chlorophenyl)-1-(3-pyridyl)-2-propen-1-ol (0.692 g, 2.8 mmol), triethylamine (3.3 ml) and 4-dimethylaminopyridine (85 g) was stirred in acetic anhydride (0.9 ml) at 25° C. for 20 h. Methanol (1 ml) was added and after 10 min the mixture was concentrated in vacuo. Ether (25 ml) was added and the ether phase was washed with saturated NaHCO$_3$ solution (3×15 ml) and dried over MgSO$_4$. Evaporation of the solvent gave 0.725 g (90%) of the title compound, which was used in the palladium catalyzed amination according to Example 16.

PREPARATION OF END COMPOUNDS

In the examples below NMR and mass spectra are in accordance with the structures indicated.

EXAMPLE 1

(Z)-3-(3-chlorophenyl)-N,N-dimethyl-3-(3-pyridyl)allylamine oxalate (Method A)

A solution of 3-(3-chlorophenyl)-N,N-dimethyl-3-hydroxy-3-(3-pyridyl)-propylamine (4.45 g, 15 mmol) in 5 ml glacial acetic acid and 3.3 ml concentrated sulphuric acid was refluxed for 1 h. After cooling 25 ml water was added and pH adjusted with concentrated ammonia solution to 9.5. The mixture was extracted with ether. The ether phase was dried and evaporated to yield 3.6 g (88%) of a brown oil. The crude product was found to hold the diastereomers in a Z/E isomeric ratio of 72/28 according to GLC. The base mixture was dissolved in 20 ml acetone and one equivalent of oxalic acid in acetone was added to precipitate the title compound. This was recrystallized from ethanol to give a white crystalline substance with less than 0.5% of E-isomer according to GLC and NMR. M.p. 171°–174° C.

EXAMPLE 2

(Z)-3-(4-chlorophenyl)-N,N-dimethyl-3-(3-pyridyl)allylamine oxalate (Method C)

A solution of crude 3-chloro-1-(4-chlorophenyl)-1-(3-pyridyl)-1-propene (40 mmol) was added to dimethylamine (18.0 g, 400 mmol) in 25 ml methylene chloride at 10° C. After stirring at room temperature for 1.5 h 25 ml water were added, the phases separated and the solvent removed from the organic phase. The residue was taken up in ether and extracted with dilute hydrochloric acid to pH 4.5. The aqueous phase was made alkaline, extracted with ether and the solvent removed. The residual oil (6.8 g) was dissolved in acetone and one equivalent of oxalic acid in acetone was added. The precipitated oxalate was recrystallized twice from ethanol to give 5.1 g (35%) of pure product mainly (95%) containing the Z-isomer. M.p. 164°–168° C.

UV (0.1 M HCl): $\lambda_{max}$ 246 nm and $\lambda_{min}$ 224 nm cf 4-bromo analogue: $\lambda_{max}$ 250 nm and $\lambda_{min}$ 225 nm. Acta Pharm. Suecica 16, 299 (1979).

$^1$H-NMR (CDCl$_3$, base): δ2.23 (s, CH$_3$), 3.01 (d, allyl), 6.30 (t, vinyl), 7.0–7.6 (aromatic), 8.45 (m, 2-pyridyl) and 8.6 (dd, 6-pyridyl).

EXAMPLE 3

3-(4-Chlorophenyl)-N-methyl-3-(3-pyridyl)allylamine oxalate (Method C)

Z-isomer

The title compound was prepared in analogy with the tertiary amine according to Example 2 from the crude 3-chloro-1-(4-chlorophenyl)-1-(3-pyridyl)-1-propene and methylamine with the following exceptions. Ethanol was used as cosolvent during the amination and the crude oxalate was recrystallized from ethanol/water (3:1). The yield of pure product was 23% of mainly (97%) the Z-isomer according to HPLC and UV. M.p. 203°–204.5° C. UV (0.1 M HCl): $\lambda_{max}$ 245 nm and $\lambda_{min}$ 224 nm. (cf 4-bromoanalogue: $\lambda_{max}$ 248 nm and $\lambda_{min}$ 224 nm. Acta Pharm. Suecica 16, 299 (1979).

E-isomer

From the mother liquor of the above recrystallization a sample was purified by HPLC (reversed phase system Nucleosil 5μ, methanol-phosphate buffer pH 3.0 40+60). The methanol was evaporated and the aqueous solution was made alkaline and extracted twice with ether. After drying (MgSO$_4$) the ethereal solution was concentrated in vacuo leaving an oil having a UV spectra in accordance with the E-configuration.

UV (0.1 M HCl): $\lambda_{max}$ 219 nm and 235 nm (shoulder) cf 4-bromoanalogue $\lambda_{max}$ 220 nm and 236 nm (shoulder) Acta Pharm. Suecica 16, 299 (1979).

The compounds obtained by Examples 4–10 were prepared by Method C according to Examples 2 and 3 from the corresponding allylic alcohols after allylic rearrangement to the corresponding allylic chlorides according to Example C.

EXAMPLE 4

3-(4-Fluorophenyl)-N,N-dimethyl-3-(3-pyridyl)allylamine oxalate. 40% yield. M.p. 151°–155° C.

EXAMPLE 5

3-(4-Fluorophenyl)-N-methyl-3-(3-pyridyl)allylamine oxalate. 30% yield. M.p. 196°–198° C.

EXAMPLE 6

(E)-3-(2-Bromophenyl)-N,N-dimethyl-3-(3-pyridyl)allylamine oxalate. M.p. 148°–149° C.

EXAMPLE 7

(E)-3-(2-Bromophenyl)-N-methyl-3-(3-pyridyl)allylamine oxalate. M.p. 200°–202° C.

EXAMPLE 8

(Z)-3-(3-Bromophenyl)-N-methyl-3-(3-pyridyl)allylamine oxalate. 21% yield. M.p. 198°–199° C.

EXAMPLE 9

(E)-3-(2,4-Dichlorophenyl)-N,N-dimethyl-3-(3-pyridyl)allylamine oxalate. 25% yield. M.p. 167°–169° C.

EXAMPLE 10

(E)-3-(2,4-Dichlorophenyl)-N-methyl-3-(3-pyridyl)allylamine oxalate. M.p. 203°–205° C.

EXAMPLE 11

(Z)-3-(4-iodophenyl)-N,N-dimethyl-3-(3-pyridyl)allylamine oxalate (Method E)

Butyllithium (10 mmol) in 10 ml hexane was injected through a septum to a stirred solution of (Z)-3-(4-bromophenyl)-N,N-dimethyl-3-(3-pyridyl)allylamine (3.2 g, 10 mmol) in 30 ml dry tetrahydrofuran under a nitrogen atmosphere at −65° C. The deep red solution was stirred for 0.5 h at −65° C. and then iodine (2.54 g, 10 mmol) was added. The mixture was stirred for an additional 0.5 h at −65° C. and then allowed to reach room temperature during 1.5 h. Water was added, the tetrahydrofuran evaporated and the residue extracted with ether. The ether phase was washed with sodium bisulphite, dried over magnesium sulphate and evaporated to give 2.7 g of an oil. This residue was dissolved in hydrochloric acid at pH 5.9 and extracted with 1,2-dichloroethane. The organic phase was evaporated to give a residue of 1.8 g which was triturated three times with ether, leaving 1.0 g of the off-white crystalline hydrochloride. This product was converted to the base (0.7 g, 20%) and crystallized as the oxalate from ethanol/isopropyl ether. M.p. 170°–173° C.

EXAMPLE 12

3-(3-Bromophenyl)-N,N-dimethyl-3-(3-pyridyl)allylamine oxalate (Method F)

Butyllithium in hexane (10.5 mmol) was injected to a mixture of 4.34 g (10.5 mmol) dimethylaminoethyl triphenylphosphoniumbromide and 25 ml dry tetrahydrofuran at ambient temperature. After stirring for 15 min a solution of 2.62 g (10 mmol) 3-(3-bromobenzoyl)pyridine in 20 ml dry tetrahydrofuran was injected to the solution of the dark red ylide. The mixture was heated to 60° C. and stirred overnight. After cooling and addition of 75 ml 2 M hydrochloric acid the solution was extracted with 100 ml toluene. The organic layer was extracted with 50 ml 2 M hydrochloric acid. The combined aqueous phases were washed with 3×50 ml toluene, made alkaline and extracted twice with ether. Drying (MgSO$_4$) and evaporation of the ethereal phase gave 2.9 g (91%) of the base as a yellow oil. $^1$H NMR of the base in CDCl$_3$ showed the characteristic overlapping signals of the mixture of the diastereomers (Z and E forms), i.e. $\delta$2.2 ppm (singlet, methyl), 3.0 ppm (doublet, allyl), 6.3 ppm (triplet, vinyl) and 8.6 ppm (multiplet, 2,6-pyridyl). Integration of a Eu(fod)$_3$ [tris(1,1,1,2,2,3,3-heptafluoro-7,7-dimethyl-4,6-octanedionato)europium] shifted $^1$H NMR showed the Z/E isomeric ratio to be 53/47. GLC revealed no other compounds and the Z/E ratio was determined to 56/44.

Z-isomer

The base mixture (2.7 g, 8.5 mmol) was dissolved in hot acetone and 0.9 ml (10 mmol) conc. hydrochloric acid was added. The mixture was cooled and the acetone was decanted from the semisolid precipitate, which consists of 1.7 mmol pure Z-form according to GLC and NMR. The product was converted to base and then oxalate, which was recrystallized from ethanol/isopropyl ether to give 0.53 g (1.3 mmol) of the title compound. M.p. 162°–163° C.

EXAMPLE 13

(Z)-3-(4-Chlorophenyl)-N-methyl-3-(3-pyridyl)allylamine oxalate (Method G)

To 2.1 mmol crude (Z)-3-(4-chlorophenyl)-3-(3-pyridyl)-2-propenal, in a flask, was added in the following order: 0.68 g (10 mmol) methylamine hydrochloride, 10 ml methanol, 0.36 g (9 mmol) sodium hydroxide, 0.13 g (2 mmol) sodium cyanoborohydride and 5 g molecular sieves (3 Å). The mixture was stirred under nitrogen for 3 days and then 75 ml 2 M hydrochloric acid was added. After filtration the aqueous solution was made alkaline, extracted twice with ether and dried over MgSO$_4$. Evaporation gave 0.2 g (0.77 mmol) of an oil, which was dissolved in hot ethanol. Oxalic acid (0.7 mmol, 0.09 g) was added and the title compound precipitated from the solution to give 0.15 g (20%) of a white crystalline substance. M.p. 203.5°–204° C. The MS was identical with the MS for the same compound prepared according to Example 3, and HPLC showed a Z/E ratio of 95/5.

EXAMPLE 14

3-(4-Chlorophenyl)-N,N-dimethyl-3-(3-pyridyl)allylamine

To 0.25 g (1 mmol) crude 3-(4-chlorophenyl)-3-(3-pyridyl)-2-propenal, in a flask, was added in the following order: 0.73 g (9 mmol) dimethylamine hydrochloride, 10 ml methanol, 0.24 g (6 mmol) sodium hydroxide, 0.094 g (1.5 mmol) sodium cyanoborohydride and 5 g molecular sieves (3 Å). The mixture was stirred at room temperature under nitrogen for 3 days and then 100 ml methanol were added. After filtration the methanol was evaporated and the residue dissolved in a hydrochloric solution at pH 4.9 and washed with ether twice. The aqueous solution was made alkaline, extracted twice with ether and dried over MgSO$_4$. Evaporation gave 0.18 g (66%) of pure title compound as an isomeric mixture having an approximate Z/E ratio of 54/46 (NMR).

(E)-3-(4-Chlorophenyl)-N,N-dimethyl-3-(3-pyridyl)allylamine

A sample of the above Z/E mixture was eluted three times on preparative TLC plates (0.2 mm, 20×20 cm) with ethyl acetate/methanol/triethylamine (21/4/1). The lower band containing the E-isomer was collected and washed with methanol/dichloromethane. The solvent was evaporated to leave an oil having UV and $^1$H NMR in accordance with the E-configuration.

UV (0.1 M HCl): $\lambda_{max}$ 218 nm and 235 nm (shoulder). (cf 4-bromo analogue: $\lambda_{max}$ 219 nm and 237 nm (shoulder). Acta Pharm. Suecica 16, 299 (1979)). $^1$H NMR (CDCl$_3$): $\delta$2.22 (s, CH$_3$), 3.04 (d, allyl), 6.27 (T, vinyl), 7.0–7.6 (aromatic), 8.55 (dd, 6-pyridyl) and 8.6 (m, 2-pyridyl).

EXAMPLE 15

3-(4-Chlorophenyl)-N,N-dimethyl-3-(3-pyridyl)allylamine (Method H)

Palladium acetylacetonate (9.3 mg, 0.03 mmol), 1,2-bis-(diphenylphosphino)ethane (17.5 mg, 0.04 mmol) and 3-acetoxy-3-(4-chlorophenyl)-3-(3-pyridyl)-1-propene (0.211 g, 0.73 mmol) was dissolved in tetrahydrofuran (2.2 ml) at room temperature under nitrogen. A solution of dimethylamine in tetrahydrofuran (3.2 ml of a 2.5 M solution) was added. The resulting solution was warmed to 55° C. and allowed to react for 1 h and 40 min. Evaporation of the solvent and work-up by preparative TLC (SiO$_2$, ethyl acetate/hexane/triethylamine 49/49/2) gave 0.158 g (79%) of a Z/E mixture of the title compound. The Z/E ratio was determined by $^1$H NMR to 55/45.

EXAMPLE 16

Preparation of Soft Gelatin Capsules 500 g of active substance were mixed with 500 g of corn oil, whereupon the mixture was filled in soft gelatin capsules, each capsule containing 100 mg of the mixture (i.e. 50 mg of active substance).

EXAMPLE 17

Preparation of Soft Gelatin Capsules 500 g of active substance were mixed with 750 g of pea nut oil, whereupon the mixture was filled on soft gelatine capsules, each capsule containing 125 mg of the mixture (i.e. 50 mg of active substance).

EXAMPLE 18

Preparation of Tablets 50 kg of active substance were mixed with 20 kg of silicic acid of the trade mark Aerosil. 45 kg of potato starch and 50 kg of lactose were mixed therewith and the mixture was moistened with a starch paste prepared from 5 kg of potato starch and distilled water, whereupon the mixture was granulated through a sieve. The granulate was dried and sieved, whereupon 2 kg of magnesium stearate was mixed into it. Finally the mixture was pressed into tablets each weighing 172 mg.

EXAMPLE 19

Preparation of an Emulsion 100 g of active substance were dissolved in 2500 g of pea nut oil. From the solution thus obtained, 90 g of gum arabic, aroma and colouring agents (q.s.) and 2500 g of water an emulsion was prepared.

EXAMPLE 20

Preparation of a Syrup 100 g of active substance were dissolved in 300 g of 95% ethanol, whereupon 300 g of glycerol, aroma and colouring agents (q.s.) and 1000 ml of water were mixed therein. A syrup was obtained.

EXAMPLE 21

Preparation of an Injection Solution

Active substance (hydrobromide) (1 g), sodium chloride (0.8 g) and ascorbic acid (0.1 g) are dissolved in sufficient amount of distilled water to give 100 ml of solution. This solution, which contains 10 mg of active substance per ml, is used in filling ampoules, which are sterilized by heating at 120° C. for 20 minutes.

EXAMPLE 22

Preparation of Effervescing Tablets 100 g of active substance, 140 g of finely divided citric acid, 100 g of finely divided sodium hydrogen carbonate, 3.5 g of magnesium stearate and flavouring agents (q.s.) were mixed and the mixture was pressed into tablets each containing 100 mg of active substance.

EXAMPLE 23

Preparation of a Drop Solution 100 g of active substance were mixed with 300 g of ethanol, whereupon 300 g of glycerol, water to 1000 ml, aroma and flavouring agents (q.s.) and 0.1 N sodium hydroxide solution (to pH 4.5 to 5.5) was added while stirring. A drop solution was obtained.

EXAMPLE 24

Preparation of a Sustained Release Tablet 200 g of active substance were melted together with 50 g of stearic acid and 50 g of carnauba wax. The mixture thus obtained was cooled and ground to a particle size of at most 1 mm in diameter. The mixture thus obtained was mixed with 5 g of magnesium stearate and pressed into tablets each weighing 305 mg. Each tablet thus contains 200 mg of active substance.

(g) Pharmacological Tests

It is not possible by experimental means to induce depressions in laboratory animals. In order to evaluate a possible anti-depressive effect of new substances biochemical-pharmacological test methods must be resorted to. One such method, which seems to give a good indication of the potential anti-depressive effects of the test substance, is described in Europ. J. Pharmacol. 17, 107, 1972.

This method involves the measurement of the decrease in the uptake of $^{14}$C-5-hydroxytryptamine ($^{14}$C-5-HT) and $^3$H-noradrenaline ($^3$H-NA) in brain slices from mice after in vivo and in vitro administration of the test substance.

Inhibition of the uptake of $^{14}$C-5-HT and $^3$H-NA in vitro and in vivo

The test substances were administered intraperitoneally half an hour before the animals were killed. The hypothalamus was taken out, sliced and incubated in a mixture consisting of $1 \times 10^{-7}$ M of $^{14}$C-5-HT, $1 \times 10^{-7}$ M of $^3$H-NA, 5.6 mM glucose, $5 \times 10^{-5}$ M pargyline, 1.1 mM ascorbic acid and $1.3 \times 10^{-4}$ EDTANa$_2$ in 2 ml of Krebs-Henseleit buffer, pH 7.4 per 20 mg of brain slices. The incubation time was 5 minutes with 5 minutes of preincubation before the labelled amines were added. The slices were dissolved in Soluene® and the amounts of radioactive amines taken up were determined by liquid scintillation. The doses producing 50 percent decrease of the active uptake (ED$_{50}$) of $^{14}$C-5-HT and $^3$H-NA were determined by linear regression analysis of log dose response curves. Active uptake is defined as that part of the radioactive uptake which is inhibited by a high concentration of cocaine.

In the in vitro method slices of mouse midbrain were preincubated for 5 minutes with solution of the compound to be tested and then incubated as described above.

TABLE

Inhibition of neuronal uptake of 5-hydroxytryptamine and noradrenaline in slices from mouse brain

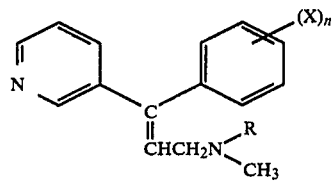

| | Compound | | | | Uptake of $^{14}$C-5-HT | | Uptake of $^3$H-NA | |
|---|---|---|---|---|---|---|---|---|
| | | | | | in vitro | in vivo ED$_{50}$ | in vitro | in vivo ED$_{50}$ |
| Example No. | X | R | isomer | salt or base | EC$_{50}$ $\mu$M | $\mu$mole/kg i.p. | EC$_{50}$ $\mu$M | $\mu$mole/kg i.p. |
| Prior art compounds | Imipramine | | | hydrochloride | 0.3 | 125 | 0.08 | 63 |
| | 4-Br | H | Z | hydrochloride | 0.1 | 15 | 1.5 | >101 (38%)$^x$ |
| | 4-Br | H | E | oxalate | 2.5 | 102 | 0.8 | 25 |
| | 4-Br | CH$_3$ | Z | hydrochloride | 1.7 | 49 | 24.4 | >98 (26%)$^x$ |
| | 4-Br | CH$_3$ | E | oxalate | 6.1 | >98 (36%)$^x$ | 6.1 | 25 |
| 3 | 4-Cl | H | Z | oxalate | 0.4 | 19 | 1.1 | 23 |
| 2 | 4-Cl | CH$_3$ | Z | oxalate | 1.1 | 34 | 1.1 | 46 |
| 5 | 4-F | H | | oxalate | 2.4 | 72 | 9 | 29 |
| 4 | 4-F | CH$_3$ | | oxalate | 4 | 115 | 29 | 72 |
| 11 | 4-I | CH$_3$ | Z | oxalate | 1.3 | 46 | >22 (33%)$^x$ | >88 (0%)$^x$ |
| 1 | 3-Cl | CH$_3$ | Z | oxalate | 2.7 | >110 (12%)$^x$ | 10 | >110 (41%)$^x$ |
| 8 | 3-Br | H | Z | oxalate | 1.4 | >102 | 0.9 | 58 |
| 12 | 3-Br | CH$_3$ | Z | oxalate | 0.9 | >98 | 4.2 | 66 |
| | 2-Br | H | E/Z 1:1 | base | 1.5 | >132 | 1.4 | 63 |
| | 2-Br | CH$_3$ | E/Z 1:1 | base | 3.5 | >126 | 2.2 | 79 |
| 7 | 2-Br | H | E | oxalate | 0.6 | 102 | 0.3 | 20 |
| 6 | 2-Br | CH$_3$ | E | oxalate | 4.2 | >98 | 2.2 | 37 |
| | 2,4-di Cl | H | E/Z 1:1 | base | 0.5 | 60 | 0.9 | 82 |
| | 2,4-di Cl | CH$_3$ | E/Z 1:1 | base | 2.7 | 42 | 11 | 63 |
| 10 | 2,4-di Cl | H | E | oxalate | 0.5 | 18 | 2.3 | 73 |
| 9 | 2,4-di Cl | CH$_3$ | E | oxalate | 1.5 | 43 | 11 | >101 |

$^x$Percentage inhibition at the highest dose (concentration) examined is given in brackets.

COMMENTS

The new compounds are potent inhibitors of the uptake of 5-HT and NA in brain slices. The secondary amine derivatives are generally more active than the tertiary amines. Of particular interest is the importance of the aromatic 4-substituent for producing selectivity of the uptake inhibition. It appears that the size of the substituent is determining this selectivity. Thus, the 4-iodo derivative is a completely selective inhibitor of the 5-HT uptake whereas the 4-chloro derivatives have comparable activity on the two uptake mechanisms. The 4-fluoro derivatives are slightly more active on the NA uptake. Furthermore, the 2-bromine derivatives cause a pronounced NA-uptake inhibition in contrast to the 2,4-dichloro substituted derivatives having marked 5-HT inhibitory properties. Thus, the selectivity of the compounds are dependent on the nature of the substituent as well as the position thereof.

The invention thus provides a class of compounds of great therapeutical value, by which it is possible to achieve therapeutical effect on the proposed "serotonin (5-HT)" and "noradrenaline" depressions. The compounds obtained can be relatively unselective (e.g. 4-F, 4-Cl), NA-selective (e.g. 2-Br, 3-Br) or 5-HT selective (e.g. 2,4-Cl$_2$, 4-I). The secondary amine derivative with a 4-chloro substituent is accordingly of great clinical interest as an unselective uptake inhibitor, which clinically should have therapeutical effect on both types of depressions.

BEST MODE OF CARRYING OUT THE INVENTION

The compound 3-(2,4-dichlorophenyl)-N-methyl-3-(3-pyridyl)allylamine oxalate and its salts, processes for preparing said compound, pharmaceutical preparations and methods of employing said compound in therapy represent the best mode of carrying out the invention known at present.

INDUSTRIAL APPLICABILITY

The invention is useful in the chemical and pharmaceutical industry and in health care.

We claim:

1. A compound of the formula

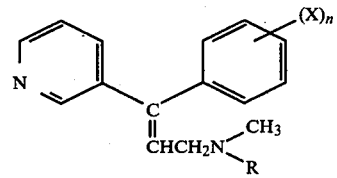

or a pharmaceutically acceptable salt thereof, in which R is H or CH$_3$, n is 1 or 2 and X is F bound in any position to the phenyl group.

2. A compound of the formula

[Structure: 3-pyridyl-C(=CHCH2N(CH3)R)-phenyl-(X)n]

or a pharmaceutically acceptable salt thereof, in which R is H or CH₃, n is 1 or 2 and X is I bound in any position to the phenyl group.

3. A compound of the formula

[Structure: 3-pyridyl-C(=CHCH2N(CH3)R)-phenyl-(X)n]

or a pharmaceutically acceptable salt thereof, in which R is H or CH₃, n is 1 and X is 2-Br or 3-Br.

4. A compound of the formula

[Structure: 3-pyridyl-C(=CHCH2N(CH3)R)-phenyl-(X)n]

or a pharmaceutically acceptable salt thereof, in which R is H, n is 1 and X is chlorine bound at the 3- or 4-position, said compound being in the form of the substantially resolved geometrical isomers in the E-form or the Z-form.

5. A compound or salt according to claim 1, 2 or 3 in the form of a geometrical isomer.

6. A compound or salt according to claim 5 wherein the pyridyl group and the amino function are in cis configuration.

7. A compound according to claims 1, 2 or 3 characterized in that R is H, or a pharmaceutically acceptable salt thereof.

8. A compound or salt according to claim 1 or 2 characterized in that n is 1.

9. A compound according to claim 1 or 2 characterized in that n is equal to 2.

10. A compound according to claims 1, 2 or 3 characterized in that a group X is bound in the 2-position to the phenyl group.

11. The compound according to claim 3 which is 3-(2-bromophenyl)-N,N-dimethyl-3-(3-pyridyl)-allylamine or a pharmaceutically acceptable salt thereof.

12. The compound according to claim 3 which is 3-(2-bromophenyl)-N-methyl-3-(3-pyridyl)-allylamine or a pharmaceutically acceptable salt thereof.

13. The compound according to claim 2 which is 3-(4-iodophenyl)-N,N-dimethyl-3-(3-pyridyl)-allylamine, or a pharmaceutically acceptable salt thereof.

14. The compound according to claim 1 which is 3-(4-fluorophenyl)-N-methyl-3-(3-pyridyl)-allylamine, or a pharmaceutically acceptable salt thereof.

15. A compound of the formula Z-3-(4-chlorophenyl)-N-methyl-3-(3-pyridyl)-allylamine, or a pharmaceutically acceptable salt thereof.

16. A compound of the formula 3-(4-fluorophenyl)-N,N-dimethyl-3-(3-pyridyl)-allylamine, or a pharmaceutically acceptable salt thereof.

17. A pharmaceutical preparation which comprises as active ingredient a therapeutically effective amount of at least one compound of the formula

[Structure: 3-pyridyl-C(=CHCH2N(CH3)R)-phenyl-(X)n]

or a pharmaceutically acceptable salt thereof, in which R is H or CH₃, n is 1 or 2 and X is F bound in any position to the phenyl group, in association with a pharmaceutically acceptable carrier.

18. A pharmaceutical preparation which comprises as active ingredient a therapeutically effective amount of at least one compound of the formula

[Structure: 3-pyridyl-C(=CHCH2N(CH3)R)-phenyl-(X)n]

or a pharmaceutically acceptable salt thereof, in which R is H or CH₃, n is 1 or 2 and X is I bound in any position to the phenyl group, in association with a pharmaceutically acceptable carrier.

19. A pharmaceutical preparation which comprises as active ingredient a therapeutically effective amount of at least one compound of the formula

[Structure: 3-pyridyl-C(=CHCH2N(CH3)R)-phenyl-(X)n]

or a pharmaceutically acceptable salt thereof, in which R is H or CH₃, n is 1 and X is 2-Br or 3-Br, in association with a pharmaceutically acceptable carrier.

20. A pharmaceutical preparation which comprises as active ingredient a therapeutically effective amount of at least one compound of the formula

[Structure: 3-pyridyl-C(=CHCH2N(CH3)R)-phenyl-(X)n]

or a pharmaceutically acceptable salt thereof, in which formula R is H, n is 1 and X is chlorine bound at the 3- or 4-position, said compound being in the form of the substantially resolved geometrical isomers in the E-form or the Z-form, in association with a pharmaceutically acceptable carrier.

21. A method for the treatment of depression characterized in administering to a host suffering from such an ailment a therapeutically effective amount of a compound of the formula:

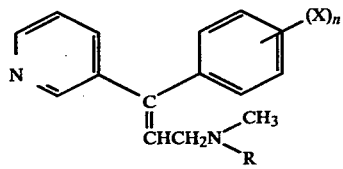

or a pharmaceutically acceptable salt thereof, in which R is H or CH$_3$, n is 1 or 2 and X is F bound in any position to the phenyl group.

22. A method for the treatment of depression characterized in administering to a host suffering from such an ailment a therapeutically effective amount of a compound of the formula:

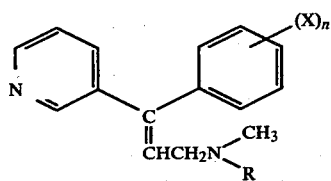

or a pharmaceutically acceptable salt thereof, in which R is H or CH$_3$, n is 1 or 2 and X is I bound in any position to the phenyl group.

23. A method for the treatment of depression characterized in administering to a host suffering from such an ailment a therapeutically effective amount of a compound of the formula:

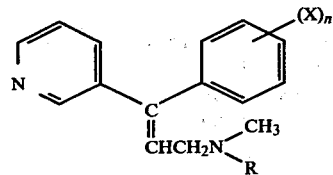

or a pharmaceutically acceptable salt thereof, in which R is H or CH$_3$, n is 1 and X is 2-Br or 3-Br.

24. A method for the treatment of depression characterized in administering to a host suffering from such an ailment a therapeutically effective amount of a compound of the formula

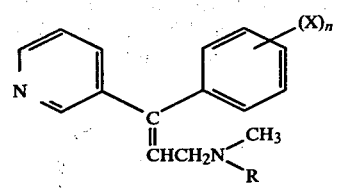

or a pharmaceutically acceptable salt thereof, in which R is H, n is 1 and X is chlorine bound at the 3- or 4-position, said compound being in the form of the substantially resolved geometrical isomers in the E-form or the Z-form.

* * * * *

UNITED STATES PATENT AND TRADEMARK OFFICE
CERTIFICATE OF CORRECTION

PATENT NO. : 4,418,065

DATED : November 29, 1983

INVENTOR(S) : Thomas Hogberg et al

It is certified that error appears in the above-identified patent and that said Letters Patent is hereby corrected as shown below:

itle Page, Item 56, 10th line, "4/1975" should read --4/1976--;

itle Page, Item 57, 7th line of ABSTRACT", "phramaceutical" should read --pharmaceutical--;

Column 2, line 47, "pharmacetically" should read --pharmaceutically--;

Column 16, line 34, "(T, vinyl)" should read --(t, vinyl)--.

Signed and Sealed this

Twenty-eighth Day of February 1984

[SEAL]

Attest:

GERALD J. MOSSINGHOFF

Attesting Officer       Commissioner of Patents and Trademarks